United States Patent
Wu et al.

(10) Patent No.: US 11,964,068 B2
(45) Date of Patent: Apr. 23, 2024

(54) ATOMIC OXYGEN AND OZONE CLEANING DEVICE HAVING A TEMPERATURE CONTROL APPARATUS

(71) Applicant: Applied Materials, Inc., Santa Clara, CA (US)

(72) Inventors: Banqiu Wu, San Jose, CA (US); Eli Dagan, Sunnyvale, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 459 days.

(21) Appl. No.: 17/200,408

(22) Filed: Mar. 12, 2021

(65) Prior Publication Data

US 2022/0288259 A1    Sep. 15, 2022

(51) Int. Cl.
*A61L 2/20*    (2006.01)
*A61L 2/10*    (2006.01)

(52) U.S. Cl.
CPC .............. *A61L 2/202* (2013.01); *A61L 2/10* (2013.01); *A61L 2202/11* (2013.01); *A61L 2202/122* (2013.01)

(58) Field of Classification Search
CPC ........ A61L 2/202; A61L 2/10; A61L 2202/11; A61L 2202/122
See application file for complete search history.

(56) References Cited

U.S. PATENT DOCUMENTS

2001/0000477 A1* 4/2001 Harada ............. H01L 21/67028
427/534
2006/0223315 A1* 10/2006 Yokota ............. H01L 21/67115
118/724

(Continued)

FOREIGN PATENT DOCUMENTS

CN    111359994 A     7/2020
DE    19924058 A1 * 11/2000 ....... H01L 21/02046

(Continued)

OTHER PUBLICATIONS

PCT Notification of Transmittal of the International Search Report and the Written Opinion of the International Searching Authority for International Application No. PCT/US2022/016332; dated Jun. 9, 2022.

*Primary Examiner* — Sean E Conley
*Assistant Examiner* — Justin Hwang
(74) *Attorney, Agent, or Firm* — Patterson + Sheridan, LLP

(57) ABSTRACT

Embodiments of the present disclosure relate to an oxygen cleaning chamber with UV radiation generator temperature control and a method of atomic oxygen cleaning a substrate. The atomic oxygen cleaning chamber includes a process chamber and a cooling chamber coupled to the process chamber and a divider sealingly separating the process chamber from the cooling chamber. An ultraviolet (UV) radiation generator is disposed in the cooling chamber and provides UV radiation through the divider into the process chamber. A gas distribution assembly distributes ozone over an upper surface of a pedestal in the process chamber and a coolant distribution assembly distributes cooling gas into the cooling chamber to cool the UV radiation generator. By actively cooling the UV radiation generator, a higher intensity UV radiation at a stable wavelength is produced, i.e., without wavelength drift normally associated with high power UV radiation generator outputs.

13 Claims, 3 Drawing Sheets

(56) References Cited

U.S. PATENT DOCUMENTS

| | | | | |
|---|---|---|---|---|
| 2007/0295012 A1* | 12/2007 | Ho | ............... | H01L 21/67109 |
| | | | | 62/56 |
| 2007/0295355 A1* | 12/2007 | Ikuta | ............ | H01L 21/67028 |
| | | | | 134/1 |
| 2015/0283279 A1* | 10/2015 | Lott | ............ | G01F 1/76 |
| | | | | 250/428 |
| 2020/0098556 A1 | 3/2020 | Wu et al. | | |
| 2020/0297004 A1* | 9/2020 | Alzeer | ............ | A23L 3/001 |

FOREIGN PATENT DOCUMENTS

| | | | |
|---|---|---|---|
| JP | H03283429 A | 12/1991 | |
| KR | 10-2002-0060909 A | 7/2002 | |

\* cited by examiner

ATOMIC OXYGEN AND OZONE CLEANING DEVICE HAVING A TEMPERATURE CONTROL APPARATUS

BACKGROUND

Field

Embodiments of the present disclosure generally relate to apparatuses and methods to clean equipment. More particularly, embodiments of the present disclosure relate to an oxygen cleaning chamber with UV radiation generator temperature control and a method of atomic oxygen cleaning a substrate.

Description of the Related Art

In the cleaning of semiconductor devices, it is often desirable to remove contaminants from surfaces of a substrate, thus leaving clean surfaces. Absent cleaning, contaminants may be present that will negatively impact semiconductor device performance. Cleanliness of semiconductor devices and chamber components impacts product yield, chamber uptime, and customer cost.

Most substrate cleaning techniques utilize oxygen-containing cleaning agents exposed to ultraviolet (UV) radiation to oxidize the surfaces of the substrate. Atomic oxygen compared to other oxygen-containing cleaning agents has the highest reaction rate and oxidizing capability such that the surfaces of the substrate are cleaned at a greater rate for greater throughput. However, atomic oxygen has a short life and once formed, will combine with $O_2$ and other molecules of the oxygen-containing cleaning agent. Additionally, increasing the efficiency of forming the atomic oxygen depends on the intensity of UV radiation from a UV radiation generator. However, increasing the intensity will increase the heat emitted from the UV radiation generator leading to emission spectrum shift of the UV radiation.

Accordingly, there is a need for an improved oxygen cleaning chamber and a method of atomic oxygen cleaning a substrate.

SUMMARY

In one embodiment, an atomic oxygen cleaning chamber is provided. The atomic oxygen cleaning chamber includes a process chamber. The atomic oxygen cleaning chamber further includes a cooling chamber coupled to the process chamber and a divider sealingly separating the process chamber from the cooling chamber. The atomic oxygen cleaning chamber further includes an ultraviolet (UV) radiation generator disposed in the cooling chamber and operable to provide UV radiation through the divider into the process chamber and a pedestal disposed in the process chamber. The atomic oxygen cleaning chamber further includes a gas distribution assembly operable to distribute ozone over an upper surface of the pedestal and a coolant distribution assembly operable to distribute cooling gas into the cooling chamber to cool the UV radiation generator.

In another embodiment, an atomic oxygen cleaning chamber is provided. The atomic oxygen cleaning chamber includes a process chamber. The atomic oxygen cleaning chamber further includes a cooling chamber coupled to the process chamber and a divider sealingly separating the process chamber from the cooling chamber. The atomic oxygen cleaning chamber further includes an ultraviolet (UV) radiation generator disposed in the cooling chamber and operable to provide UV radiation through the divider into the process chamber and a pedestal disposed in the process chamber. The atomic oxygen cleaning chamber further includes a gas distribution assembly operable to distribute ozone over an upper surface of the pedestal and a coolant distribution assembly. The coolant distribution assembly includes a coolant gas inlet, a coolant gas outlet, and a coolant gas source operable to distribute cooling gas across the cooling chamber, and a coolant pump operable to force cooling gas across the cooling chamber to the coolant gas outlet.

In yet another embodiment, a method of atomic oxygen cleaning a substrate is provided. The method of atomic oxygen cleaning a substrate includes positioning a substrate on an upper surface of a pedestal disposed in a process chamber. The method of atomic oxygen cleaning a substrate further includes flowing ozone into the process chamber and distributing the ozone over the substrate. The method of atomic oxygen cleaning a substrate further includes flowing cooling gas into a cooling chamber to maintain a temperature of a UV radiation generator below a predetermined temperature. The method of atomic oxygen cleaning a substrate further includes providing radiation at a wavelength between about 240 nanometers (nm) to about 310 nm from the UV radiation generator disposed in the cooling chamber to the ozone disposed in the processing chamber.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments of the present disclosure generally relate to apparatuses and methods to clean equipment. More particularly, embodiments of the present disclosure relate to an oxygen cleaning chamber with UV radiation generator temperature control and a method of atomic oxygen cleaning a substrate. The atomic oxygen cleaning chamber includes a process chamber. The atomic oxygen cleaning chamber further includes a cooling chamber coupled to the process chamber and a divider sealingly separating the process chamber from the cooling chamber. The atomic oxygen cleaning chamber further includes an ultraviolet (UV) radiation generator disposed in the cooling chamber and operable to provide UV radiation through the divider into the process chamber and a pedestal disposed in the process chamber. The atomic oxygen cleaning chamber further includes a gas distribution assembly operable to distribute ozone over an upper surface of the pedestal and a coolant distribution assembly operable to distribute cooling gas into the cooling chamber to cool the UV radiation generator.

Figure 1A:
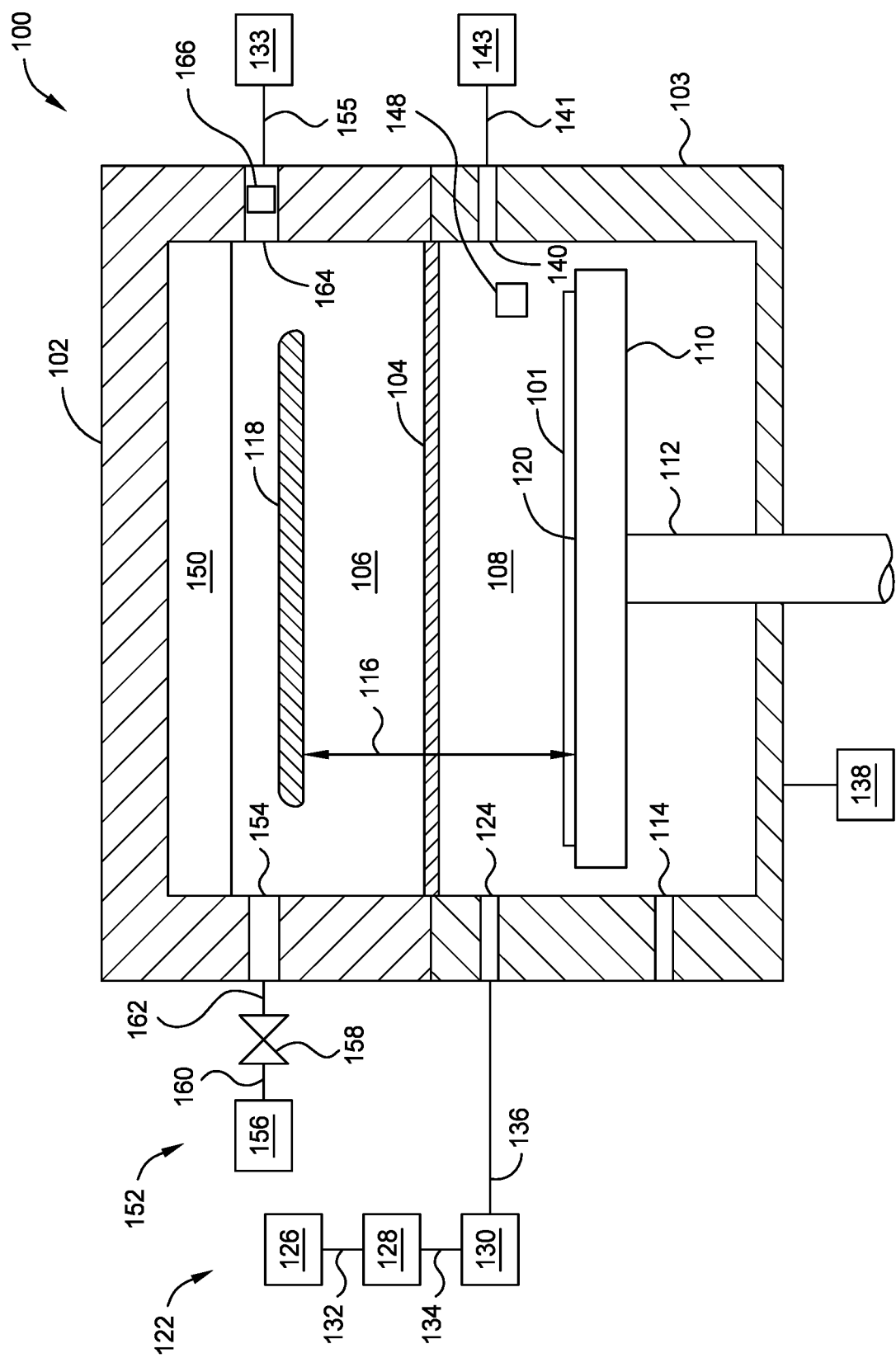
FIGS. 1A and 1B are schematic cross-sectional views of an atomic oxygen cleaning chamber according to embodiments.
Figure 1B:
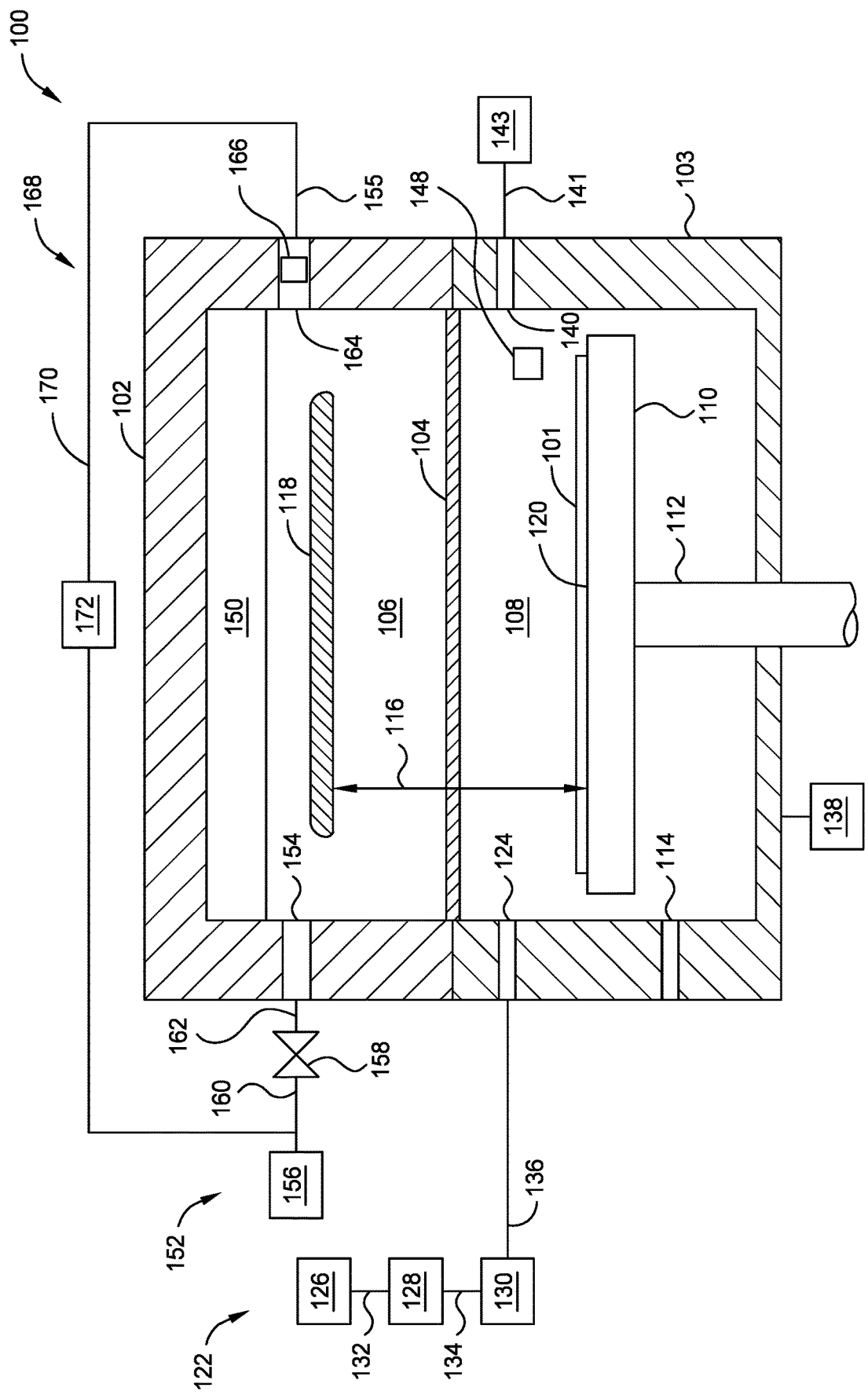

FIGS. 1A and 1B are schematic cross-sectional views of an atomic oxygen cleaning chamber 100. The atomic oxygen cleaning chamber 100 is suitable for cleaning a substrate using atomic oxygen. The atomic oxygen cleaning chamber 100 of FIG. 1B includes a coolant recirculation assembly 168. The atomic oxygen cleaning chamber 100 of FIG. 1B includes all elements of the atomic oxygen cleaning chamber 100 of FIG. 1A with the addition of the coolant recirculation assembly 168. The atomic oxygen cleaning chamber 100 includes a cooling chamber 102 and a process chamber 103. The cooling chamber 102 is coupled to the process chamber 103. The cooling chamber 102 and the process chamber 103 are separated by a divider 104. The cooling chamber 102 is stacked adjacent to the process chamber 103. The divider 104 provides a seal to separate and isolate the process chamber 103 from the cooling chamber 102. The cooling chamber 102 and the process chamber 103 may be two separate bodies stacked adjacently. The cooling chamber 102 and the process chamber 103 may be a single body. The cooling chamber 102 includes a cooling volume 106. The cooling volume 106 is the space defined by the cooling chamber 102 and the divider 104. The process chamber 103 includes a processing volume 108. The processing volume 108 is the space defined by the process chamber 103 and the divider 104.

The processing volume 108 includes a pedestal 110 for supporting a substrate 101 within the process chamber 103. The pedestal 110 is supported by a stem 112. The pedestal 110 is movably disposed in the processing volume 108 by the stem 112 which extends through the process chamber 103. The stem 112 is connected to a lift system (not shown) that moves the pedestal 110 between a processing position (as shown) and a transfer position that facilitates substrate transfer to and from the processing volume 108 through a slit valve 114 formed though the process chamber 103. The processing position corresponds to a distance 116 from an ultraviolet (UV) radiation generator 118 to an upper surface 120 of the pedestal 110.

The process chamber 103 includes a gas distribution assembly 122. The gas distribution assembly 122 includes a gas inlet 124, an oxygen-containing gas source 126, an ozone ($O_3$) generator 128, and a flow controller 130. The gas inlet 124 is disposed in the process chamber 103. The ozone generator 128 is in fluid communication with an oxygen-containing gas source 126 via a first conduit 132. The ozone generator 128 is capable of generating ozone from the oxygen-containing gas and sustaining the ozone at a desired pressure and concentration. The flow controller 130, such as a mass flow control (MFC) device, in fluid communication with the ozone generator 128 via a second conduit 134 controls a flow rate of ozone from the ozone generator 128. The atomic oxygen cleaning chamber 100 includes a controller 138. The controller 138 includes a central processing unit (CPU), a memory, and support circuits for the CPU. The controller 138 is in communication with the flow controller 130 to control the flow rate of the ozone entering the processing volume 108. The controller 138 enables control of the operating parameters and operations, such as a method 200 of atomic oxygen cleaning a substrate 101, for the atomic oxygen cleaning chamber 100.

The ozone is flowed from the ozone generator 128 into the process chamber 103 via the gas inlet 124 and the flow controller 130. The gas inlet 124 is connected to the flow controller 130 via a third conduit 136. The flow of ozone distributes over the upper surface 120 of the pedestal 110. A gas outlet 140 is disposed in the process chamber 103. A pump 143 is coupled to the gas outlet 140 for controlling the pressure within the process volume 108 and exhausting byproducts from the processing volume 108 through the gas outlet 140 via a fourth conduit 141. The processing volume 108 includes a UV intensity sensor 148 disposed therein. The UV intensity sensor 148 is operable to measure the UV intensity of the UV radiation discharged by the UV radiation generator 118.

The UV radiation from the UV radiation generator 118 is able to pass from the cooling volume 106 to the processing volume 108 through the divider 104. The divider 104 retains the heat dissipated by the UV radiation generator 118 in the cooling chamber 102 such that the temperature of the processing chamber 103 can be more effectively controlled. The divider 104 is a transparent material operable to allow UV radiation to pass through. For example, the divider 104 is fused quartz, fused silica, combinations thereof, or other suitable materials.

The UV radiation generator 118 is disposed in the cooling volume 106. The UV radiation generator 118 may include one or more UV radiation sources. The UV radiation sources may each be a low pressure mercury lamp. The UV radiation generator 118 generates UV radiation. The UV radiation generator 118 may include lamps, LED emitters, or other UV emitters configured to discharge radiation at about 240 nm to about 310 nm wavelength. For example, the UV radiation generator 118 discharges radiation with a wavelength at about 253 nm.

Ozone from the ozone generator 128 distributed over the surface of the substrate 101 is exposed to the UV radiation from the UV radiation generator 118 and converted to oxygen gas ($O_2$) and atomic oxygen (O). The oxygen gas and atomic oxygen oxidize inorganic materials, such as hydrocarbons, on the surface of the substrate 101 producing carbon dioxide ($CO_2$) and water ($H_2O$) as byproducts. The pump 143 exhausts the byproducts from the processing volume 108. Atomic oxygen compared to other oxygen-containing cleaning agents has the highest reaction rate and oxidizing capability such that the surface of the substrate 101 is cleaned at a greater rate for greater throughput. For example, atomic oxygen can oxidize $SO_2$ to $SO_3$ instantly on the surface of the substrate 101. The $SO_3$ may be easily removed from the substrate 101 by a water-based cleaning step. The $SO_3$ may be removed by the pump 143 or may be removed in a later cleaning process. The removal of $SO_2$ by atomic oxygen cleaning the substrate 101 slows down haze defect accumulation. As stated above, atomic oxygen has a short life and once formed will combine with $O_2$ and other molecules. The ozone generator 128 is capable of continuously providing ozone to the processing volume 108 such that the UV radiation generated by the UV radiation generator 118 converts the ozone into atomic oxygen in situ. In situ atomic oxygen generation in the processing volume 108 provides a high concentration of atomic oxygen to the surface of the substrate 101. The coolant recirculation assembly 168 maintains the UV radiation generator 118 at a constant temperature to prevent emission spectrum drift which will cause the intensity of the UV radiation to decrease. The coolant recirculation assembly 168 improves the intensity of the UV radiation from the UV radiation generator 118 to increase efficiency of the atomic oxygen cleaning process. The distance 116 from the UV radiation generator 118 to the upper surface 120 of the pedestal 110 controls the concentration of atomic oxygen provided to the surface of the substrate 101.

The cooling chamber 102 includes a reflector 150. The reflector 150 is disposed in the cooling volume 106 and coupled to the cooling chamber 102. The reflector 150 is operable to reflect the UV radiation discharged by the UV radiation generator 118 such that the UV radiation is more efficiently directed into the processing volume 108 through the divider 104. In one embodiment, the reflector 150 is disposed above the UV radiation generator 118.

The cooling chamber 102 includes a coolant distribution assembly 152. The coolant distribution assembly 152 includes a coolant gas inlet 154, a coolant source 156, and a coolant flow controller 158. The coolant gas inlet 154 is disposed in the cooling chamber 102. The coolant flow controller 158, such as a mass flow control (MFC) device, is in fluid communication with the coolant source 156 via a first coolant conduit 160. The coolant flow controller 158 controls a flow rate of cooling gas from the coolant source 156. The coolant source 156 includes a cooling gas such as air, nitrogen gas ($N_2$), or other suitable gases. The divider 104 prevents the cooling gas from mixing with the ozone deposed in the processing volume 108. The cooling gas from the coolant source 156 travels through the coolant flow controller 158 and to the coolant gas inlet 154 via a second coolant conduit 162. The cooling gas exiting the coolant gas inlet 154 flows over the UV radiation generator 118 to a coolant gas outlet 164, thus removing heat generated by the UV radiation generator 118.

The coolant distribution assembly 152 is utilized to control the temperature of the UV radiation generator 118. To increase the efficiency of forming the atomic oxygen, it is desirable to have a high intensity of UV radiation from the UV radiation generator 118 at a wavelength of about 254 nm that enters the processing volume 108. To increase the intensity of the UV radiation emitted by the UV radiation generator 118, electrical power provided to the UV radiation generator 118 is increased. The increase in electrical power will cause the UV radiation generator 118 to emit heat. The heat dissipation will cause emission spectrum drift of the UV radiation. The emission spectrum drift will cause the intensity of the UV radiation at 254 nm to decrease. The coolant distribution assembly 152 flows the cooling gas in the cooling volume 106 to maintain the cooling volume 106 between about 30° C. and about 40° C. The cooling gas from the coolant source 156 flows over the UV radiation generator 118 to maintain the UV radiation generator 118 at a constant temperature.

A temperature sensor 166 provides information used to determine the effectiveness of cooling the UV radiation generator 118. In one example, the temperature sensor 166 obtains information from which the temperature of the cooling gas exiting the cooling volume 106 can be determined and used to determine the temperature of the cooling volume 106 and/or the UV radiation generator 118. The temperature sensor 166 is in communication with the coolant flow controller 158 and the controller 138. The flow rate can be adjusted by the coolant flow controller 158 based on the metric to either increase or decrease the temperature of the UV radiation generator 118. Additionally, the UV intensity sensor 148 is in communication with the coolant flow controller 158 and the controller 138. Based on the UV intensity readings of the UV intensity sensor 148, the flow rate of the coolant entering the cooling volume 106 can be adjusted by the coolant flow controller 158 to either increase or decrease the temperature based on the operational status of the UV radiation generator 118 or the amount of UV radiation sensed by the UV intensity sensor 148. One or both of the temperature sensor 166 and the UV intensity sensor 148 may be disposed in the atomic oxygen cleaning chamber 100.

As shown in FIG. 1A, which can be combined with other embodiments described herein, the atomic oxygen cleaning chamber 100 includes a coolant pump 153. The coolant pump 153 is coupled to the coolant gas outlet 164 for controlling the cooling gas pressure within the cooling volume 106 and exhausting excess cooling gas from the cooling volume 106 through the coolant gas outlet 164 via a third coolant conduit 155.

As shown in FIG. 1B, which can be combined with other embodiments described herein, the atomic oxygen cleaning chamber 100 includes a coolant recirculation assembly 168. The coolant recirculation assembly 168 is coupled between the coolant gas inlet 154 and the coolant gas outlet 164. The coolant recirculation assembly 168 includes a coolant flow line 170 and a heat exchanger 172. The coolant flow line 170 is in fluid communication with the coolant gas outlet 164 via the third coolant conduit 155. A pump (not shown) forces the cooling gas to exit the cooling volume 106 and enter the coolant recirculation assembly 168. The cooling gas flows through the coolant flow line 170 to the heat exchanger 172. The heat exchanger 172 removes heat from the cooling gas to the outside environment or to another cooling fluid. The cooling gas flows from the heat exchanger 172 through the coolant flow line 170 to the coolant flow controller 158 where the recirculated cooling gas is reintroduced to the cooling volume 106. The cooling gas is supplied to the coolant flow line 170 from the coolant source 156 via the first coolant conduit 160. The cooling gas travels through the coolant flow controller 158 and to the coolant gas inlet 154 via a second coolant conduit 162.

Figure 2:
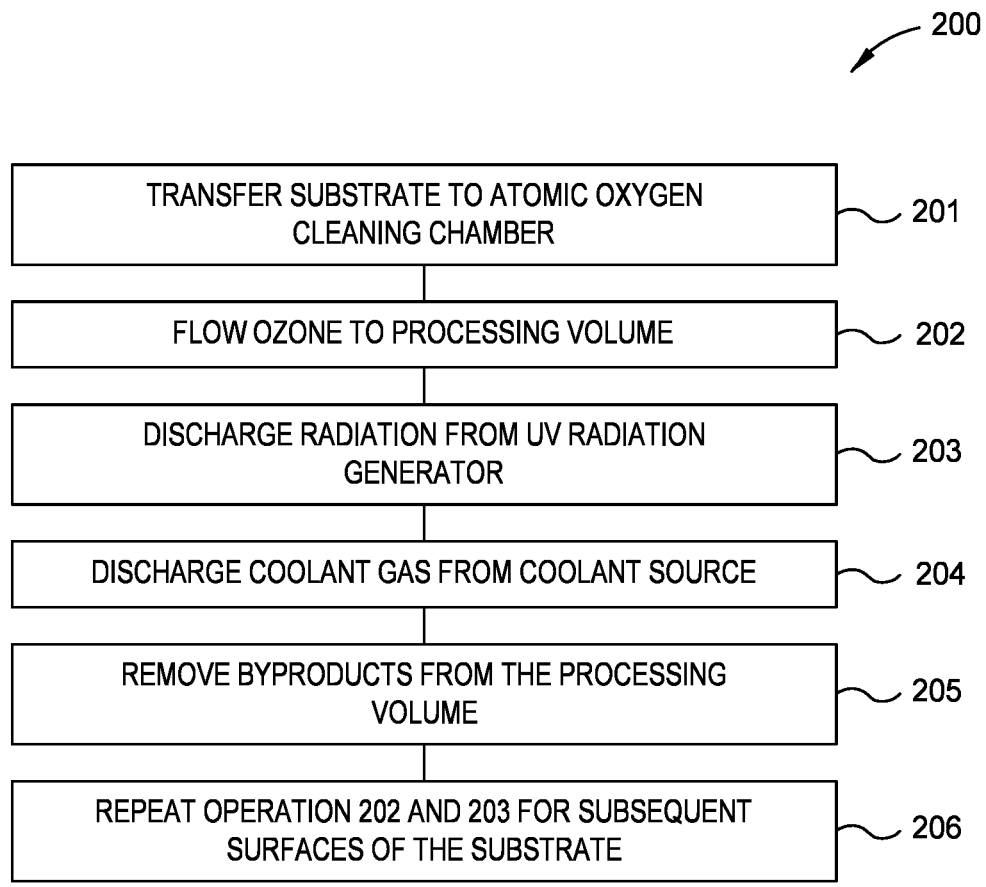
FIG. 2 is a flow diagram of a method of atomic oxygen cleaning a substrate according to embodiments.

FIG. 2 is a flow diagram of a method 200 of atomic oxygen cleaning a substrate 101. To facilitate explanation, FIG. 2 will be described with reference to FIG. 1A and FIG. 1B. However, it is to be noted that atomic oxygen cleaning chambers other than the atomic oxygen cleaning chamber 100 may be utilized to perform the method 200.

At operation 201, a substrate 101 is transferred to an atomic oxygen cleaning chamber 100. The atomic oxygen cleaning chamber 100 includes a process chamber 103 and a cooling chamber 102. The substrate 101 enters a processing volume 108 of the process chamber 103 through a slit valve 114. The substrate 101 is positioned on a pedestal 110 disposed in the processing volume 108. A first surface of the substrate 101 is oriented towards an ultraviolet (UV) radiation generator 118 disposed in a cooling volume 106 of the cooling chamber 102. A distance 116 from the UV radiation generator 118 to an upper surface 120 of the pedestal 110 is about 7 millimeters (mm) to about 30 mm.

At operation 202, a flow of ozone is provided to the processing volume 108. The ozone gas is flowed into the processing volume 108 at a rate of about 50 sccm to about 20000 sccm. The pressure in the processing volume 108 is maintained between about 0 psi to about 15 psi. The flow of ozone distributes over the first surface of the substrate 101 in the processing volume 108. The flow rate of the ozone entering the processing volume 108 is controlled by a flow controller 130 in communication with a controller 138.

At operation 203, the UV radiation generator 118 discharges radiation. The radiation passes through a divider 104 from the cooling volume 106 of the cooling chamber 102 to the processing volume 108. The UV radiation generator 118 is configured to discharge radiation having a wavelength between about 240 nm to about 310 nm. The flow of ozone distributed over the first surface of the substrate 101 in the processing volume 108 is exposed to the radiation and is converted to oxygen gas ($O_2$) and atomic oxygen (O). The oxygen gas and atomic oxygen oxidize organic materials, such as hydrocarbons, on the first surface of the substrate 101 producing carbon dioxide ($CO_2$) and water ($H_2O$) as byproducts.

At operation 204, cooling gas enters the cooling volume 106. The cooling gas may be provided from a coolant source 156 and/or may be recirculated through a heat exchanger 172 to the cooling volume 106. The cooling gas is discharged from the coolant source 156 to the cooling volume 106 through a coolant gas inlet 154. The cooling gas flows over the UV radiation generator 118 to maintain the cooling volume 106 and/or the UV radiation generator 118 below a predetermined temperature. The predetermined temperature is between about 30° C. and about 40° C. The flow rate of the cooling gas into the cooling volume 106 is between about 1 lpm and about 10 lpm. The pressure in the cooling volume 106 is about 0 psi to about 15 psi. When the atomic oxygen cleaning chamber 100 includes a coolant pump 153, the cooling gas is removed from the cooling volume 106 with the coolant pump 153. When the atomic oxygen cleaning chamber 100 includes a coolant recirculation assembly 168, the cooling gas travels through a coolant flow line 170 to a heat exchanger 172. The heat exchanger 172 removes heat from the cooling gas prior to reentry into the cooling volume 106 through the coolant gas inlet 154.

The temperature of the UV radiation generator 118 and/or the cooling volume 106 are controlled with a controller 138, a coolant flow controller 158, and one or both of a temperature sensor 166 and a UV intensity sensor 148. The temperature sensor 166 and/or the UV intensity sensor 148 are in communication with the controller 138. The temperature sensor 166 and the UV intensity sensor 148 are operable to obtain a metric from which the temperature of the cooling gas or the UV intensity of the radiation, respectively can be determined. The temperature sensor 166 and the UV intensity sensor 148 send a signal to the controller 138 relaying the temperature and intensity information. The temperature of the cooling gas or the UV intensity of the radiation may be used to ascertain the temperature of the UV radiation generator 118. The controller 138, in communication with the coolant flow controller 158 is operable to control the flow rate of the cooling gas flowed into the cooling chamber 102 based on the measurements of the temperature sensor 166 and the UV intensity sensor 148 so as to maintain the UV radiation generator 118 at a desired temperature.

At operation 205, the byproducts are removed from the processing volume 108. A pump 143 is coupled to a gas outlet 140 for exhausting byproducts from the processing volume 108 through the gas outlet 140. At optional operation 206, operations 202, 203, 204, and 205 are repeated for subsequent surfaces of the substrate 101. For example, the substrate 101 may be flipped such that an opposite side of the substrate 101 may be exposed in the process chamber 103. At the conclusion of the method 200, the substrate 101 may be removed from the atomic oxygen cleaning chamber 100 for further processing.

In summation, an atomic oxygen cleaning chamber with UV radiation generator temperature control and a method of atomic oxygen cleaning a substrate are described herein. By actively cooling the UV radiation generator, the UV radiation generator may be operated to produce higher intensity UV radiation at a stable wavelength, i.e., without wavelength drift normally associated with high power UV radiation generator outputs. The high intensity output enables more atomic oxygen compared to other oxygen-containing cleaning agents for fast reaction rates and oxidizing capabilities, such that the surface of the substrate is cleaned quickly and efficiently. The atomic oxygen cleaning chamber includes an ozone generator that continuously provides ozone to the processing volume such that radiation generated by a UV radiation generator converts the ozone into atomic oxygen in situ.

While the foregoing is directed to examples of the present disclosure, other and further examples of the disclosure may be devised without departing from the basic scope thereof, and the scope thereof is determined by the claims that follow.

What is claimed is:

1. An atomic oxygen cleaning chamber, comprising:
a process chamber;
a cooling chamber coupled to the process chamber;
a divider sealingly separating the process chamber from the cooling chamber;
an ultraviolet (UV) radiation generator disposed in the cooling chamber and outside of the process chamber, and operable to provide UV radiation through the divider into the process chamber;
a pedestal disposed in the process chamber;
a gas distribution assembly operable to distribute ozone over an upper surface of the pedestal;
a coolant distribution assembly operable to distribute cooling gas into the cooling chamber to cool the UV radiation generator, the coolant distribution assembly comprising a coolant gas inlet and a coolant gas outlet disposed in the cooling chamber; and
a coolant recirculation assembly, the coolant recirculation assembly comprising a coolant flow line coupling the coolant gas outlet of the cooling chamber with the coolant gas inlet of the cooling chamber, and operable to recirculate the cooling gas from the coolant gas outlet of the cooling chamber to the cooling gas inlet of the cooling chamber without entering the process chamber.

2. The atomic oxygen cleaning chamber of claim 1, further comprising a temperature sensor positioned to provide a metric indicative of a temperature of the UV radiation generator.

3. The atomic oxygen cleaning chamber of claim 2, further comprising a UV intensity sensor disposed in the process chamber, the UV intensity sensor operable to provide a metric indicative of UV intensity of the UV radiation discharged from the UV radiation generator.

4. The atomic oxygen cleaning chamber of claim 3, further comprising a controller, the controller in communication with the coolant distribution assembly and operable to control a flow rate of the cooling gas entering the cooling chamber based on the temperature sensor and the UV intensity sensor.

5. The atomic oxygen cleaning chamber of claim 1, wherein the coolant distribution assembly further comprises:
a heat exchanger coupled between the coolant gas inlet and the coolant gas outlet of the cooling chamber.

6. The atomic oxygen cleaning chamber of claim 1, wherein the gas distribution assembly comprises:
a gas inlet disposed in the process chamber, the gas inlet coupled to the gas distribution assembly; and
a gas outlet disposed in the process chamber, the gas outlet coupled to a pump.

7. The atomic oxygen cleaning chamber of claim 6, wherein the gas distribution assembly further comprises:

an oxygen-containing gas source;

an ozone generator in communication with the oxygen-containing gas source; and a flow controller, the flow controller operable to control a flow rate of the ozone entering the process chamber, the flow controller in communication with the ozone generator.

8. The atomic oxygen cleaning chamber of claim 1, further comprising a coolant pump coupled to an outlet formed in the cooling chamber.

9. The atomic oxygen cleaning chamber of claim 1, wherein a reflector is disposed in the cooling chamber and disposed above the UV radiation generator.

10. The atomic oxygen cleaning chamber of claim 1, wherein the divider is a fused silica material.

11. The atomic oxygen cleaning chamber of claim 1, wherein the pedestal includes a processing position corresponding to a distance from the UV radiation generator to the upper surface of the pedestal.

12. An atomic oxygen cleaning chamber, comprising:
a process chamber;
a cooling chamber coupled to the process chamber;
a divider sealingly separating the process chamber from the cooling chamber;
an ultraviolet (UV) radiation generator disposed in the cooling chamber and outside of the process chamber, and operable to provide UV radiation through the divider into the processing chamber;
a pedestal disposed in the process chamber;
a gas distribution assembly operable to distribute ozone over an upper surface of the pedestal;
a coolant distribution assembly, the coolant distribution assembly having a coolant gas inlet, a coolant gas outlet, and a coolant source operable to distribute cooling gas across the cooling chamber, and a coolant pump operable to force cooling gas across the cooling chamber to the coolant gas outlet; and
a coolant recirculation assembly, the coolant recirculation assembly comprising a coolant flow line coupling the coolant gas outlet of the cooling chamber with the coolant gas inlet of the cooling chamber, and operable to recirculate the cooling gas from the coolant gas outlet of the cooling chamber to the coolant gas inlet of the cooling chamber without entering the process chamber.

13. The atomic oxygen cleaning chamber of claim 12, wherein the coolant distribution assembly further comprises:
a heat exchanger coupled between the coolant gas inlet and the coolant gas outlet of the cooling chamber.

* * * * *